United States Patent [19]

Jakobson et al.

[11] Patent Number: 5,169,964
[45] Date of Patent: Dec. 8, 1992

[54] PROCESS FOR PREPARING HIGH PURITY EPICHLOROHYDRIN

[75] Inventors: Gerald Jakobson; Werner Siemanowski, both of Rheinberg, Fed. Rep. of Germany

[73] Assignee: Deutsche Solvay-Werke GmbH, Solingen, Fed. Rep. of Germany

[21] Appl. No.: 333,008

[22] Filed: Apr. 4, 1989

[30] Foreign Application Priority Data

Apr. 6, 1988 [DE] Fed. Rep. of Germany ....... 3811524

[51] Int. Cl.$^5$ ............................................. C07D 301/32
[52] U.S. Cl. ..................................................... 549/541
[58] Field of Search ......................................... 549/541

[56] References Cited

U.S. PATENT DOCUMENTS 4,134,797 1/1979 Ozero .................................. 549/541
4,304,639 12/1981 Hardy et al. ......................... 549/541

FOREIGN PATENT DOCUMENTS 1210777 2/1966 Fed. Rep. of Germany .
1021417 3/1966 United Kingdom .

Primary Examiner—C. Warren Ivy
Assistant Examiner—Ba K. Trinh
Attorney, Agent, or Firm—Foley & Lardner

[57] ABSTRACT

The present invention relates to a process for preparing ultrapure epichlorohydrin from epichlorohydrin containing technical impurities, by fractional distillation under particular conditions, preferably with continuous operation, that yield a product of very high purity and very low content of halogenated hydrocarbons. Epoxy resins made with such ultrapure epichlorohydrin are especially well suited for use in fabricating electrical components and microchips.

14 Claims, No Drawings

PROCESS FOR PREPARING HIGH PURITY EPICHLOROHYDRIN

BACKGROUND OF THE INVENTION

The present invention relates to a process for preparing high-purity epichlorohydrin from epichlorohydrin containing technical impurities by distillation in a column which is equipped with an evaporation or heating device located at or near the sump of the column, the preparation of high-purity epichlorohydrin being improved by certain processing techniques and/or apparatus features or apparatus combinations.

German Auslegeschrift 1,210,777 discloses a process for the preparation of epichlorohydrin by dehydrochlorination of 1,2-dichloropropan-3-ol with alkaline agents in aqueous medium at elevated temperature. According to Example 1, paragraph 2, crude epichlorohydrin is rectified via a twenty-plate column, yielding a "pure" product with a boiling point of 115° to 116° C. in addition to unreacted dichloropropanol. However, even after rectification, the epichlorohydrin obtained in this manner still contains interfering impurities in the form, inter alia, of halogenated hydrocarbons and the like. Elimination of such impurities is important where the epichlorohydrin is to be used for making ultrapure resins for use in electronic components or devices, microchips and the like.

OBJECTS OF THE INVENTION

One object of the present invention is to provide a process for preparing epichlorohydrin of enhanced purity with respect to technical grade reagent.

Another object of the invention is to provide a process for preparing epichlorohydrin with a substantial reduction in the chlorinated hydrocarbon content with respect to technical grade epichlorohydrin.

SUMMARY OF THE INVENTION

These and other objects of the invention are achieved by providing a process for preparing high-purity epichlorohydrin from epichlorohydrin containing technical impurities, which comprises;

fractionally distilling technical epichlorohydrin in a column having at least 15 theoretical plates and which is provided with heating evaporating means located at or near the sump of the column, inlet means for introducing technical epichlorohydrin at an intermediate point in said column, and outlet means for withdrawing high-purity epichlorohydrin at a point above said inlet means;

wherein the technical epichlorohydrin is introduced into said column at a distance from said evaporation or heating means which is greater than one-tenth of the total length of the column, and the high-purity epichlorohydrin is withdrawn at a distance from said evaporation or heating means which is greater than one-third of the total length of the column.

DETAILED DESCRIPTION

The invention provides a process for the preparation of high-purity epichlorohydrin from epichlorohydrin containing technical impurities by distillation in a column equipped with an evaporation or heating device located at or near the sump of the column. The term "technical epichlorohydrin", as used herein, denotes epichlorohydrin having a purity of up to about 997 g/kg of epichlorohydrin, and normally having a chlorinated hydrocarbon content of at least 2 g/kg. Even higher purity reagent, e.g., up to about 999.1 g/kg, with respect to epichlorohydrin content, can still be considered technical grade, in the sense of being unsuitable for use in preparing resins for certain sensitive applications in electronic or microchip devices, if its content of chlorinated hydrocarbons is higher than about 0.7 g/kg.

According to the invention, technical grade epichlorohydrin is subjected to fractional distillation, preferably in a perforated-plate column, bubble-cap plate column and/or packed column. The column is equipped with an evaporation or heating device (or an evaporation or heating area or zone) located at or near the bottom of the column (or below the first plate), and is furnished with means to introduce an inlet stream at a point intermediate between the bottom and the top of the column, means to withdraw a product stream at a higher intermediate point on the column, means to withdraw a lower-boiling stream at or near the top of the column, and means to withdraw a higher-boiling stream at or near the bottom of the column.

Normally, the column will have at least 15 theoretical plates, preferably at least 20, and more preferably at least 25 plates.

The technical epichlorohydrin is fed into the column at an intermediate point along its length, at a distance from the evaporation or heating device (or the evaporation or heating area or zone) which is greater than one-tenth, preferably greater than one-quarter, of the total length of the column. High-purity epichlorohydrin is drawn off at a distance from the evaporation or heating device (or the evaporation or heating area or the evaporation zone) which is greater than one-third, preferably greater than one-half, of the total length of the column.

A lower-boiling stream (epichlorohydrin containing a higher percentage of impurities and/or low-boiling azeotropic mixtures) is continuously drawn off at the head of the column and a higher-boiling stream (epichlorohydrin containing a higher percentage of impurities and/or high-boiling azeotropic mixtures containing epichlorohydrin) is continuously drawn off at the foot of the column.

The process according to the invention is performed at a pressure in the column of 0.2 to 1.3 bar, preferably 0.5 to 1 bar or 1.05 bar. However, it is particularly advantageous to operate at normal pressure (smaller equipment costs) or under a vacuum of 0.8 to 0.98 bar (inter alia gentle evaporation of the epichlorohydrin).

The minimum distance for the inlet or inlet position(s) for the technical epichlorohydrin to be purified from the evaporation or heating device (the evaporation or heating area or the evaporation zone) depends, inter alia. on the total length of the column, the filling with certain packings and/or the minimum spacing of the perforated plates, and is, for example, in the case of very long columns or heavily or densely packed columns and the·like, greater than one-tenth of the total length of the column. It is, however, particularly expedient for this minimum distance to be greater than one-eighth or one-sixth, preferably greater than one-quarter, of the total length of the column.

According to a preferred embodiment of the process according to the invention, the technical epichlorohydrin is pre-heated to a temperature below the boiling point prior to being fed in the column. This preheating, in conjunction with the above procedural measures, is of particular importance for achieving the required degree of purity of the high-purity epichlorohydrin.

In the process according to the invention, the difference in the preheating temperature and the operational temperature in the column is not greater than 50° C., preferably not greater than 10° C. The purpose of the preheating is to bring the temperature of the technical epichlorhydrin to be fed into the column to the same or approximately the same operational temperature prevailing in the column. The term "operational temperature" refers to the temperature in about the middle region of the column.

The process according to the invention is preferably performed as a continuous process, so that the preheated technical epichlorohydrin is continuously fed into the column at a distance from the evaporation or heating device which is greater than one-tenth, preferably greater than one-quarter, of the total length of the column. While the high-purity epichlorhydrin is drawn off at a sufficient distance above the inlet position to effect the desired enhanced purity, the impurities are continuously drawn off at the head and at the sump.

The pump output for feeding the technical epichlorohydrin into the column is regulated according to the invention in such a manner that the amount fed in is equal to or approximately equal to the sum of the amounts discharged or drawn off.

The evaporation and/or heating of the epichlorohydrin in the column is preferably carried out using a circulation evaporator. According to a preferred embodiment of the process according to the invention, a distance is maintained between the inlet position(s) of the technical epichlorohydrin in the column and the outlet position(s) for the high-purity epichlorohydrin which is greater than one-fifth of the length of the column, preferably greater than one-quarter of the length of the column. The high purity epichlorhydrin is then drawn off above the inlet position(s) of the technical epichlorohydrin The process of the invention advantageously is carried out in an apparatus which comprises at least one column which is equipped with evaporation or heating means located at or near the sump of the column and at least one inlet and one or more outlet means or devices. According to the invention, the outlet position for the high-purity epichlorohydrin in the vertical distillation column is located above the inlet position of the technical epichlorohydrin. The heating or evaporation device for the column, preferably a perforated-plate column, a bubble-cap plate, and/or a packed column, is located below the inlet position(s) of the technical epichlorohydrin, The distance of the inlet position(s) for the technical epichlorohydrin from the evaporation or heating device is greater than one-tenth, preferably greater than one-quarter, based on the total length of the column, while the distance of the outlet position(s) for high-purity epichlorohydrin from the inlet position(s) of the epichlorhydrin is greater than one-fifth, preferably greater than one-quarter, of the length of the column. According to a particularly expedient embodiment, a distance was maintained between the inlet position(s) for the technical epichlorohydrin and the evaporation or heating device which was greater than one-sixth, preferably greater than one-quarter, based on the total length of the column.

The evaporation or heating device of the column preferably consists of a circulation evaporator.

A device for preheating the technical epichlorohydrin to be fed in is attached to the column. The preheating device is preferably located on or in a feed vessel or a feed device or on or in a storage vessel or a similar container which serves as a receptacle for the technical epichlorohydrin to be fed in and which is provided, preferably in its inlet device, preferably inlet tube and the like, which is attached to the column, with metering and/or closure devices, valves and the like. Furthermore, according to one embodiment, pumps, injectors and the like are located on the feed vessel or on the inlet device.

The invention further relates to the use of the high-purity epichlorohydrin, preferably prepared by the process according to the invention, for the preparation of epoxy resins for electronic components, electronic devices and microchips.

The high-purity epichlorohydrin prepared according to the present process generally has a purity of at least about 999.2 g/kg of epichlorohydrin, preferably 99.4 g/kg, more preferably 999.5 g/kg, 999.7 g/kg and even up to 999.95 g/kg. It generally has a much reduced content, e.g., at least as low as 0.5 g/kg, preferably as low as 0.3 g/kg, of halogenated hydrocarbons, or is virtually free from halogenated hydrocarbons, i.e., about at the limit of detection of sensitive instruments, or about 50 ppm by weight. Such high-purity epichlorohydrin is reacted in a manner known per se with monofunctional or polyfunctional phenols, carboxylic acids or amines, preferably aromatic amines. The resultant epoxy resins are formed or processed to produce electronic components, devices or microchips without the use of processing auxiliary agents containing chlorine ions or halogen ions or using only small amounts of such agents. The advantage of using materials with a very low halogenated hydrocarbon content in such devices is minimization of corrosion, which can occur if chlorine or other halogens are liberated by local heating or electrical decomposition of the halogenated compounds.

For continuous operation in the preparation of high-purity epichlorohydrin on the laboratory scale, a piston metering pump is preferably used for feeding technical epichlorohydrin to the column. The metering output is controlled by a regulator, preferably a level regulator, placed in the sump phase. The discharge at the head is preferably provided with a regulator, preferably a magnetically or pneumatically controlled liquid divider. The sump and product discharge has at its disposal pumps known per se, for example piston or membrane metering pumps. Evaporation devices, preferably circulation evaporation devices known per se, for example quartz electric heating rods or metal insert heating devices and the like, controlled by probes in the sump and in the regulator, are used as sump heaters or circulation evaporators.

The following example illustrates the process of the invention and the use of apparatus according to the invention, but is not limitative thereof.

APPLICATION EXAMPLE

At the height of the 8th plate (counted from the foot of the column) of a perforated-plate column having a total of 35 plates, 2.2 liters of technical epichlorohydrin with an epichlorohydrin content of 999.1 g/kg, preheated to 114° C., are introduced under normal pressure. 300 ml of a mixture of epichlorohydrin and low-boiling components are drawn off per hour at the head of the column, and 350 ml of a mixture of epichlorohydrin and high-boiling components are drawn off per hour at the sump.

At the height of the 25th plate 1550 ml of high-purity epichlorohydrin with a epichlorohydrin content of 999.7 g/kg at 116° C. are drawn off per hour.

The chlorinated hydrocarbon content of the technical epichlorohydrin is 0.7 g/kg, and of the high-purity product is 0.2 g/kg.

What is claimed is:

1. A process for preparing high-purity epichlorohydrin from epichlorohydrin containing technical impurities, which comprises the steps of:
   preheating technical epichlorohydrin to a temperature below its boiling point; and
   fractionally distilling said preheated technical epichlorohydrin at a pressure of 0.2 to 1.05 bar in a column having at least 15 theoretical plates and which is provided with heating or evaporating means located at or near the sump of the column, inlet means for introducing technical epichlorohydrin at an intermediate point in said column, and outlet means for withdrawing high-purity epichlorohydrin at a point above said inlet means,
   wherein said preheated technical epichlorohydrin is introduced into said column at a distance from said evaporation or heating means which is greater than one-tenth of the total length of the column, and the high-purity epichlorohydrin is withdrawn at a distance from said evaporation or heating means which is greater than one-third of the total length of the column,
   and wherein the temperature difference between said preheated technical epichlorohydrin introduced into the column and the operational epichlorohydrin introduced into the column and the operational temperature in the column is 50° C. or less.

2. The process of claim 1, wherein said column has at least 20 theoretical plates.

3. The process of claim 2, wherein said column has at least 25 theoretical plates.

4. The process of claim 1, wherein the technical epichlorohydrin is introduced into said column at a distance from said evaporation or heating means which is greater than one-quarter of the total length of the column.

5. The process of claim 1, wherein the high-purity epichlorohydrin is withdrawn at a distance from said evaporation or heating means which is greater than one-half of the total length of the column.

6. The process of claim 1, wherein said temperature difference is 10° C. or less.

7. The process of claim 1, wherein the preheated technical epichlorohydrin is continuously introduced into the column.

8. The process of claim 7, wherein low-boiling impurities or low-boiling azeotropic mixtures with epichlorohydrin are continuously withdrawn at the head of the column and high-boiling impurities or high-boiling azeotropic mixtures containing epichlorohydrin are continuously withdrawn at the foot of the column.

9. The process of claim 1, wherein the rate of introduction of the technical epichlorohydrin is regulated in such a manner that the amount introduced is substantially equal to the sum of the amounts discharged or withdrawn.

10. The process of claim 1, wherein the heating of the epichlorohydrin in the column is carried out by using a circulation evaporator.

11. The process of claim 1, wherein the distance between the position on the column of said inlet means and the position on the column of said outlet means is greater than one-fifth of the length of the column.

12. The process of claim 11, wherein said distance between said inlet means and said outlet means is greater than one-quarter of the length of the column.

13. The process of claim 1, wherein said pressure is 0.5 to 1 bar.

14. The process of claim 1, wherein said column is a perforated-plate column, a bubble-cap plate column or a packed column.

* * * * *